US008333720B2

(12) United States Patent
Nysaether

(10) Patent No.: US 8,333,720 B2
(45) Date of Patent: Dec. 18, 2012

(54) DEVICES AND METHODS FOR MONITORING CHEST COMPRESSIONS

(75) Inventor: Jon Nysaether, Hafrsfjord (NO)

(73) Assignee: Laerdal Medical AS, Stavanger (NO)

( * ) Notice: Subject to any disclaimer, the term of this patent is extended or adjusted under 35 U.S.C. 154(b) by 659 days.

(21) Appl. No.: 12/130,790

(22) Filed: May 30, 2008

(65) Prior Publication Data

US 2008/0300517 A1 Dec. 4, 2008

(30) Foreign Application Priority Data

May 31, 2007 (GB) .................................. 0710460.7

(51) Int. Cl.

| | |
|---|---|
| ***A61B 5/103*** | (2006.01) |
| ***A61B 5/117*** | (2006.01) |
| ***A61B 5/08*** | (2006.01) |
| ***G09B 23/28*** | (2006.01) |
| ***A61H 31/00*** | (2006.01) |
| ***A61H 31/02*** | (2006.01) |

(52) U.S. Cl. ........ 600/595; 600/529; 600/534; 600/587; 434/262; 434/265; 601/41; 601/42; 601/43; 601/44

(58) Field of Classification Search .................. 600/529, 600/534, 587, 595; 434/262, 265; 601/41–44
See application file for complete search history.

(56) References Cited

U.S. PATENT DOCUMENTS

| | | | | |
|---|---|---|---|---|
| 6,827,695 | B2 * | 12/2004 | Palazzolo et al. | 601/41 |
| 7,220,235 | B2 * | 5/2007 | Geheb et al. | 601/41 |
| 2006/0015044 | A1 * | 1/2006 | Stavland et al. | 601/41 |
| 2008/0171311 | A1 * | 7/2008 | Centen et al. | 434/265 |

FOREIGN PATENT DOCUMENTS

| | | | |
|---|---|---|---|
| EP | 1 491 175 | A1 | 12/2004 |
| EP | 1 491 176 | A1 | 12/2004 |
| WO | 00/27334 | | 5/2000 |
| WO | 02/15836 | A2 | 2/2002 |
| WO | WO 2004/037154 | A3 | 5/2004 |
| WO | WO 2006/006870 | A1 | 1/2006 |
| WO | 2007/129908 | A1 | 11/2007 |

OTHER PUBLICATIONS

Sven O. Aase and Helge Myklebust; "Compression Depth Estimation for CPR Quality Assessment Using DSP on Accelerometer Signals"; IEEE Transactions on Biomedical Engineering, vol. 49, No. 3, Mar. 2002, pp. 263-268.

A.E. Tomlinson et al.; "Compression force-depth relationship during out-of-hospital cardiopulmonary resuscitation"; Resuscitation (2007) 72, pp. 364-370.

* cited by examiner

*Primary Examiner* — Jeffrey G Hoekstra
*Assistant Examiner* — Devin Henson
(74) *Attorney, Agent, or Firm* — Dorsey & Whitney LLP

(57) ABSTRACT

A method for monitoring chest compressions using a compression member includes measuring a force exerted by the compression member, measuring a displacement of the compression member, providing a chest stiffness function representing the relationship between force and displacement based on values derived from the measured force and the measured displacement, and analyzing linearity of the chest stiffness function. Embodiments of the invention also include devices for performing the method.

14 Claims, 4 Drawing Sheets

DEVICES AND METHODS FOR MONITORING CHEST COMPRESSIONS

CROSS-REFERENCE TO RELATED APPLICATION

This application claims the benefit of United Kingdom patent application No. 0710460.7 filed May 31, 2007 entitled "Monitoring of chest compressions," which application is hereby incorporated by reference in its entirety.

TECHNICAL FIELD

This invention relates to devices and methods for monitoring chest compressions.

BACKGROUND OF THE INVENTION

CPR feedback systems have recently gained attention as a method for improving the quality of CPR on a cardiac arrest patient. Such systems typically measure the compression depth and rate during chest compressions, compare the measurements with accepted Guideline limits (such as those defined by the American Heart Association in 2005) and give verbal or visual feedback to the rescuer if, for instance, compression depth does not meet the accepted value of 38 mm-50 mm (1.5-2 inches).

A system for giving feedback on compressions typically consists of a sensor pad to be placed on the patient's chest. The sensor pad may contain an accelerometer and optionally a force sensor. The compression depth measurement is usually based on a double integration of acceleration. An additional force measurement can help in signal processing to remove accelerometer offset (see Aase, et. al. 2002), and can also be used to give feedback on incomplete release, as disclosed in EP 1491176 A1.

However, although current Guidelines specify a depth range for compressions, there is no direct relationship between compression depth and CPR efficacy that has been proven to be valid for all individuals.

Human bodies have various forms and sizes, and the same compression depth may not be equally efficient in a large as in a small individual. This uncertainty is qualitatively accounted for in adult CPR Guidelines, where it is acknowledged that a larger individual may require more and a smaller individual may require less compression depth than the recommended value. For children, no definite depth target exist, and the rescuer is advised to compress a certain portion of the chest height of the cardiac arrest patient (see American Heart Association 2005).

However, the acceleration based technology of most CPR feedback systems only measures the stroke length of compressions. The technology is therefore not suitable to assess the size of the patient and compensate compression depth accordingly. In addition, if the patient is placed on a compliant mattress, current systems will detect the entire movement of the chest surface and not only the dimensional change of the chest which is relevant for CPR. Thus, the depth reported by the feedback system will be too large, and the rescuer may falsely believe that she is compressing deep enough.

Many feedback systems give a warning if the rescuer does not release all force from the chest during compressions. This feedback is often based on a measurement of the minimum force alone, or the force in combination with a crude estimation of "chest compliance" to estimate compression depth such as in patent application EP 1491176 A1. However, since the force/depth characteristics for small displacements of the chest vary significantly among individuals, and because the stiffness generally increases progressively with depth, the actual leaning depth associated with such measurements may be quite uncertain.

Accordingly, there is a need for improved chest compression monitoring that accounts for different individual body types and the motion of an underlying surface.

DETAILED DESCRIPTION

Figure 1:
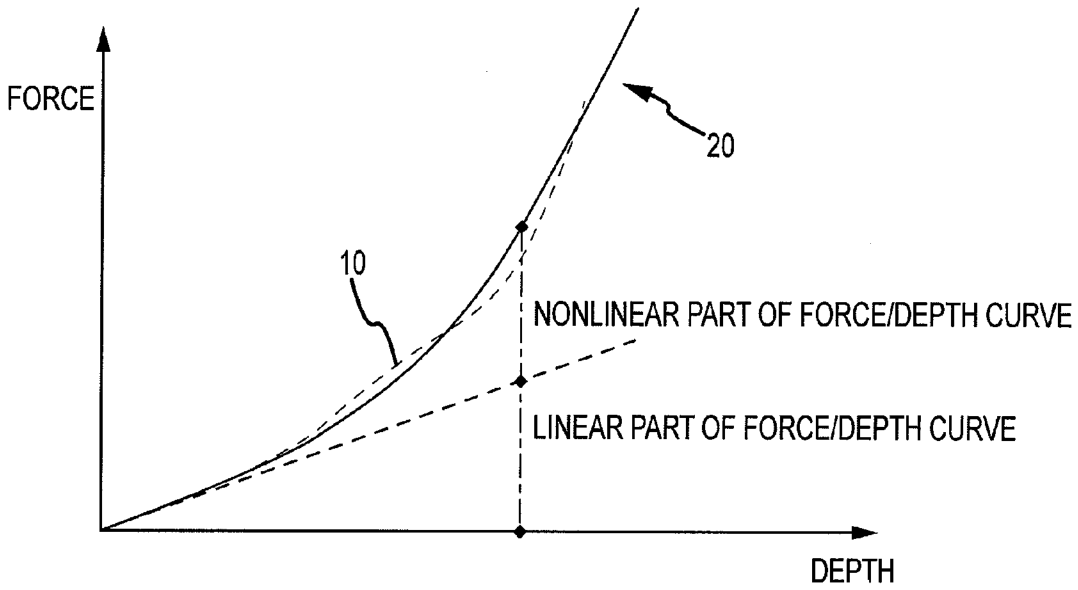
FIG. 1 depicts a parameterized measured force-depth curve according to an embodiment of the present invention.

Embodiments of the present invention may provide individualized feedback on the magnitude of delivered chest compressions by utilizing a threshold for giving feedback based on characteristic properties of the chest and also on the properties of the backing surface. Embodiments of the invention provide an indication of efficient chest compressions based on displacement and force measurement. The non-linear part of the force vs. displacement curve is used to indicate the efficacy of the chest compressions. Certain details are set forth below to provide a sufficient understanding of embodiments of the invention. However, it will be clear to one skilled in the art that embodiments of the invention may be practiced without various of these particular details. In some instances, well-known equipment, circuits, control signals, timing protocols, and software operations have not been shown in detail in order to avoid unnecessarily obscuring the described embodiments of the invention.

When performing chest compressions, the chest may need to reach a predetermined level of compression before the compression force is transmitted to the blood vessels and blood circulation is achieved. In the embodiments of the invention, a level of compression (expressed by a determined force exerted on the chest by and/or displacement of a compression member) which leads to adequate blood circulation will be referred to as "efficient compression."

Several models simulate the chest behavior under compression. Curves representing force vs. displacement show that the relationship between force and displacement is linear for small deflections and non-linear for larger deflections. For low deflections, most of the force is used only to bend the rib cage, and this linear force is therefore not efficient in pressing on the heart and generating blood pressure. It is generally at higher compression depths, where the force/displacement relationship becomes non-linear, where there is actually a generation of blood pressure and resulting flow. Accordingly, it may only the non-linear part of the compression force that is efficient in generating adequate circulation.

Since the depth or force at which the force/depth relationship (which may be a measure of chest stiffness) becomes non-linear varies from individual to individual, a measurement of chest compression based mainly on displacement of a compression member (stroke length) and/or compression force on the patient may not be able to appropriately determine whether a compression is "efficient" in generating circulation.

Embodiments of the present invention provide methods and devices for monitoring chest compressions performed using a compression member. An embodiment of a method according to the present invention includes measuring force exerted by the compression member and displacement of the compression member, then defining a chest stiffness function representing a relationship between force and displacement using the measured values. The linearity of the chest stiffness function is then analyzed, and a transition between linear and non-linear behavior of the function may be identified.

An elastic force-depth curve and damping can be calculated using a variety of methods, including the method described in Arbogast et al (2006) which generally describes measuring force and depth synchronously, and depth is differentiated to find velocity, for instance by subtracting two subsequent depth samples and dividing by the difference in sampling time. Due to the damping properties of the chest, the force at a given depth during compression (F1) will differ from the force at the same depth during decompression (F2). Assume that the difference (hysteresis) in force F1-F2 is caused by a damping force (Fd) being proportional to the speed of the chest. Based on the measured speed (v) and force difference (F1-F2), a damping constant can be calculated. The elasticity (stiffness) of the rib cage, assumed to being equal for compression and decompression, can now be found by subtracting the damping force from the measured force. Leaning depth is found by measuring the leaning force and the stiffness for low deflections, for instance for depths up to 10 mm.

For the following discussion, the following functions are used—a chest stiffness function F(x), a stiffness k(x) and an incremental chest stiffness g(x), where F(x) is the elastic part of the compression force and x is compression depth relative to the neutral position of the chest. The neutral position is the position to where the chest will recoil and come to rest if no force is applied:

Stiffness: $k(x)=F(x)/x$

Incremental stiffness: $g(x)=dF(x)/dx$

The functions above are provided to assist in describing and understanding embodiments of the invention. The theory and equations are not intended to limit embodiments of the invention.

Embodiments of the invention analyze linearity of the chest stiffness function F(x) to monitor chest compressions. The chest stiffness function can be analyzed in several ways, for example, in one embodiment of the invention non-linearity is analyzed by calculating the progressivity of the chest, here defined as the ratio of stiffness or force measured at two different levels of compression. Tomlinson et al (2006) defined progressivity as Ψ=F38/2F19, where F38 and F19 are the forces required to reach 38 and 19 mm depth, respectively.

Since the force at zero compression depth by definition is 0, the ratio of the force measured at two different depths will be related to the second derivative of the force with respect to depth or incremental stiffness. Measurements of three or more force-depth points may be combined in some embodiments to estimate higher order derivatives of force or other, related measures. The force at each level can for instance be calculated as the average of the corresponding measured forces from a predetermined number of previous compressions.

Another embodiment for analyzing determining non-linearity of the chest stiffness function is to define it in terms of a depth at which the stiffness k(x) or the incremental stiffness g(x) have increased by a certain factor relative to the value at low deflections.

Yet another embodiment of a method to analyze non-linearity of the chest stiffness function is to fit a parametrized function to a measured force-depth curve, for instance a polynomial, exponential or spline function. The parameters describing the function can then be calculated from previous compressions, and used to calculate feedback relevant parameters. The parameters may also be temporarily or permanently stored by the system The force-depth relationship can for instance be parameterized by the function $F(x)=k_1x+k_2/2x^2$, which is characterized by the parameters $k_1$ and $k_2$. Here, $k_2$ is a calculated second derivative of the chest stiffness function.

The force-depth relationship may alternately or additionally parameterized by the function F(x)=F0 (exp(x/x0)−1), which is characterized by the parameters F0 and x0.

FIG. 1 depicts a measured force/depth curve 10, shown as a dotted line. The measured force/depth curve 10 can be parameterized, for instance using a exponential or polynomial function shown as parameterized curve 20. Based on the parameterized curve 20, characteristic properties of chest non-linearity can be assessed. These properties can be compared to predetermined thresholds for acceptable compression magnitude and used as a basis to give feedback to a rescuer.

Embodiments of the invention provide an indication of efficient chest compression based on the results of the linearity analysis, where the degree of non-linearity indicates if a chest compression is indicated as efficient or non-efficient. In one embodiment, determination of non-linearity which exceeds a given threshold will lead to indication of efficient chest compression and determination of linearity or non-linearity which does not exceed the threshold will lead to indication of non-efficient chest compression. Accordingly, in one embodiment, a determination of non-linearity leads to indication of efficient chest compression and a determination of linearity leads to indication of non-efficient chest compression.

Non-linear stiffness of the chest under compression is determined in embodiments of the invention based on force and depth measurements during CPR. The measurements may be taken with a CPR sensor logging compression force and depth. Feedback may be provided according to a predetermined set of rules. The feedback system can for instance be integrated in a defibrillator or be a stand-alone system. Feedback can for instance be verbal or visual.

Values which may be derived from the non-linear function in some embodiments include:

a) Depth threshold for adequate compression magnitude b) Force threshold for adequate compression magnitude c) Depth or force threshold for feedback on incomplete release (leaning).

d) Rib break or collapse of the chest e) Patient group (pediatric or adult)

f) Presence of a mattress underneath the patient.

A depth threshold for adequate compression magnitude can for instance be given by the depth at which the stiffness or incremental stiffness of the chest attains a certain value, or reaches a certain factor of the stiffness as measured at some predefined depth. This depth is likely to be much lower for small chests than for large chests. Thus, this measure can also be used to estimate the size of a patient's chest. In an embodiment of the invention, adequate compression depth is indicated by the system if the calculated stiffness k(x) at the obtained depth is more than twice as high as the stiffness measured for low deflections, for instance up to 10-15 mm depth.

The depth at which this occurs will here be termed the stiffening point of the chest. Additional criteria can also be applied to modify or override this threshold, for instance that minimum 38 mm depth and minimum 20 kg force shall be required to indicate adequate compression depth.

In another embodiment, adequate compression magnitude may be indicated when the non-linear part of the depth (see FIG. 2), exceeds a certain threshold, for instance 20 mm, and a 'press deeper' message may be issued in some embodiments when the non-linear depth is below the threshold.

A force threshold for adequate compression magnitude can for instance be related to the non-linear portion of the force, or in other words the force which causes non-linear displacement of the compression member. This can be expressed as the measured force minus the linear extrapolation of the force-displacement curve for low deflections. Thus, a "press harder" feedback message may be given if the non-linear portion of the force does not exceed a predefined value, for instance 10 kg. The linear portion of the force can be assessed by determining the chest stiffness for small compression depths, for instance the stiffness calculated at 10 mm compression depth.

As discussed above, the clinical relevance of this criterion may be that the linear part of the force can be assumed to stem from bending of the rib cage. Thus, it is only the remaining, non-linear part of the force which actually presses on the heart and thus generates blood pressure. If the non-linear portion of the force is lower than a certain limit, it can be expected that the chest compressions are not efficient in generating the necessary blood pressure and flow.

Figure 2:
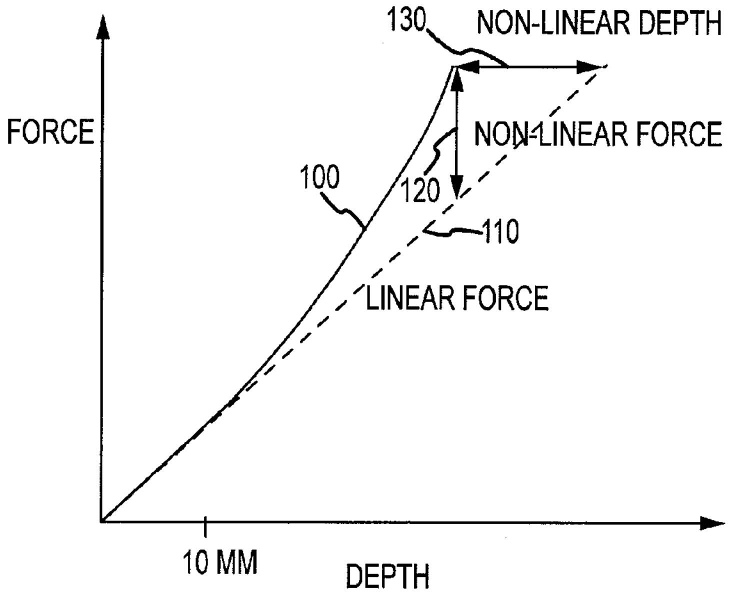
FIG. 2 depicts a force-depth curve and shows a definition of the non-linear parts of the force and depth curve according to an embodiment of the present invention.

FIG. 2 is schematic drawing of a force-depth curve 100 illustrating how a non-linear part of the force is defined. A linear portion of the force is estimated by a linear line 110. At a given depth, a difference between the linear force and the force-depth curve 100 gives the non-linear force 120. Similarly, a difference between a depth on the force depth curve and a depth given by the linear force 110 is the non-linear depth 130.

Instead of force, the pressure on the chest may be estimated in some embodiments and be a basis for giving feedback. The pressure on the chest may be estimated by dividing the force by a typical chest area. This chest area may be modified to adapt the characteristics of each individual by assuming that the chest area is proportional to, for example, the square of the chest size as described above.

A threshold for giving feedback on leaning can for instance be based on a portion of the force needed to reach a certain depth or force, or to reach a certain level of non-linearity. In an embodiment, leaning feedback or indication on leaning is given whenever the minimum force on the chest between two compressions is more than 10% of the force needed to reach a specific compression point. This point can for instance be the depth×where the calculated stiffness k(x) becomes more than twice as high as the stiffness measured at 15 mm depth.

Figure 3:
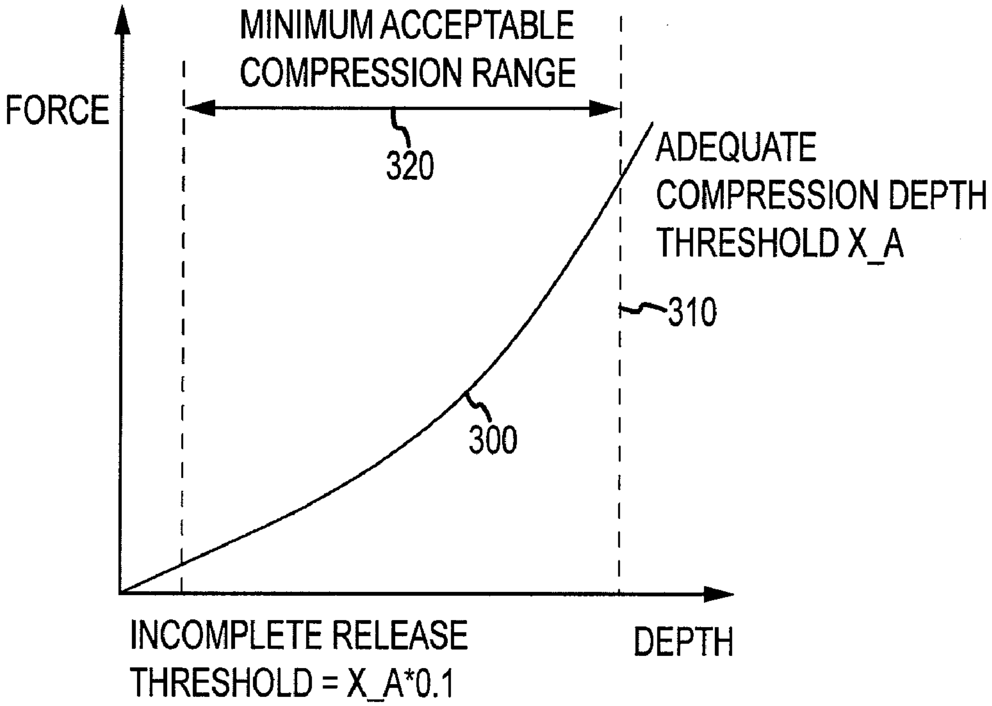
FIG. 3 depicts a force-depth curve and demonstrates use of leaning thresholds according to an embodiment of the present invention.

FIG. 3 depicts a force-depth curve 300 and schematically illustrates how, by choosing a leaning threshold as a portion of the depth or force required to reach an adequate compression magnitude 310, a minimum range of compression 320 can be defined. Appropriate corrective feedback is given whenever the compression does not exceed the indicated range in either direction. The adequate depth threshold can for instance be defined as the stiffening point of the chest.

During CPR, ribs may break or the chest may literally collapse due to the mechanical impact of the compressions. This may result in a softening of the chest for low deflections. At the same time, a chest collapse will shift the neutral point of the chest downwards, and tend to increase the force for the same stroke length at high compression levels. In combination or separately these two effects may lead to a higher chest progressivity which may be detected by the system and used to give appropriate feedback or modify feedback thresholds.

A criterion for detecting the patient category with regards to age (adult or pediatric) can for instance be based on comparing the measured progressivity to typical properties for the various age groups. Using their definition of progressivity, Tomlinson et al (2006) found that the progressivity of adults was typically 1.4, with very few being over 2. Since children are smaller and softer, they are expected to have a higher progressivity, In piglets with properties resembling children of 2-3 years, the progressivity may typically be around 2. By measuring the progressivity of the patient, or in any other manner determining the non-linearity of the force/depth relationship e.g. as mentioned above, it may be possible to determine if the patient is a child or an adult. This information may be used to change settings between pediatric and adult settings.

Figure 4:
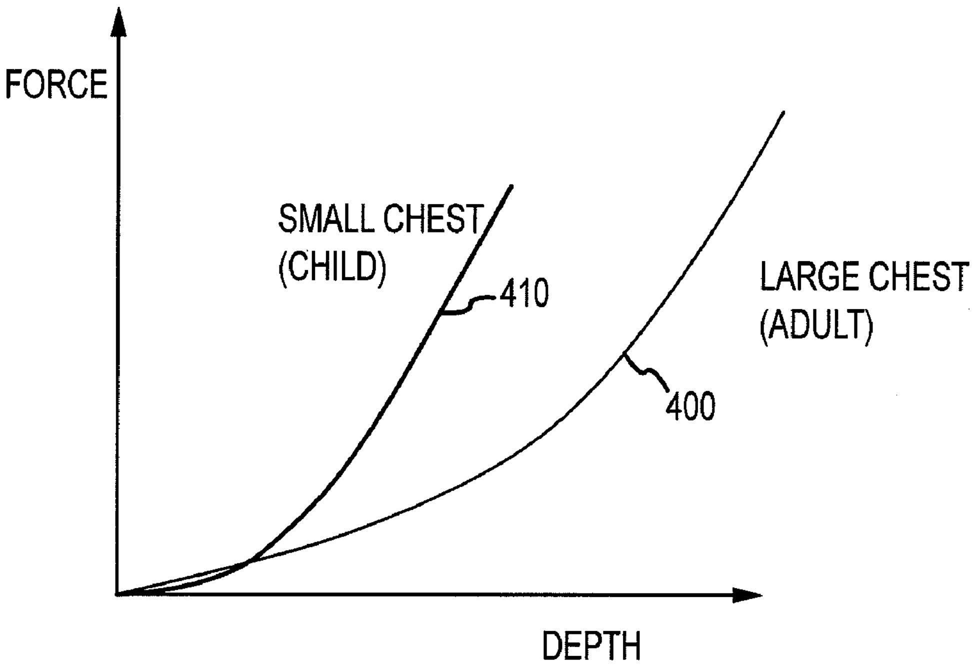
FIG. 4 depicts force-depth curves for different patient types according to an embodiment of the present invention.

FIG. 4 depicts examples of non-linear force/depth relationships for adults 400 and children 410. Children will typically have lower stiffness for low deflections, but the stiffness will increase much more rapidly with depth. By comparing measures of chest non-linearity, for instance the stiffening point, to typical ranges for children and adults, it can be determined if the patient is a child or an adult.

A criterion for distinguishing between subjects lying on surfaces with different stiffness and, for example, detecting the presence of a mattress underneath the patient can be based on the parameters characterizing the progressivity of the chest. Typically, the measured force/depth relationship of a body lying on a mattress will be linear (stiffness constant) up to much higher depths than when lying on a firm surface. The stiffness of the surface under the patient can thus be determined to a certain degree by the method according to embodiments of the present invention. Thus, if the measured progressivity of the chest, for instance the ratio of the force needed to reach 38 mm to the force needed to reach 19 mm depth is significantly lower than typical values for a body on a firm surface, the detection system will raise a flag that the person is probably lying on a mattress. Based on this information, the feedback system may give the user a warning that the patient is lying on a mattress and that feedback on depth may be uncertain.

If a mattress is detected, the system may alternatively switch to another mode of giving feedback, for instance from a depth criterion to a force based criterion where the linear part of the curve is subtracted. In case of a mattress, this will be a relevant criterion because mattresses may often be very linear in their characteristics.

Figure 5:
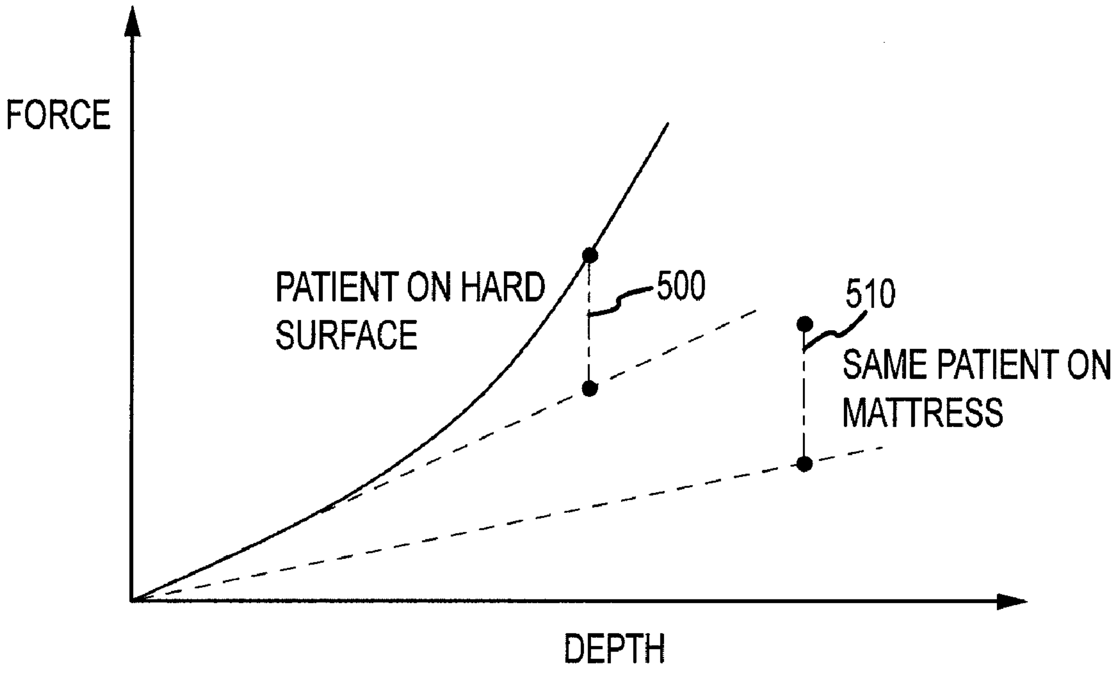
FIG. 5 depicts force-depth curves for patients lying on different surfaces according to an embodiment of the present invention.

FIG. 5 illustrates how, when a patient is placed on a mattress, a large part of the measured compression depth will be due to compression of the mattress and not deflection of the chest. Since the mattress typically has a linear force/depth profile, the non-linear part of the force or depth 500, 510 will however be approximately the same for the same level of chest deflection. By basing the feedback on non-linear parameters instead of depth, the effect of the mattress can thus be cancelled out.

Additional information can be obtained in some embodiments by calculating the moving mass of the chest. For instance, if there is a mattress beneath the patient, the moving mass will in general be higher since the whole body is moving up and down in the bed. The estimated mass can then be used as an alternative, supplementary criterion to give feedback on the presence of a mattress Mass can be calculated by correlating the force and acceleration, specifically at the beginning of a compression where both the damping and elastic forces are low.

Figure 6:
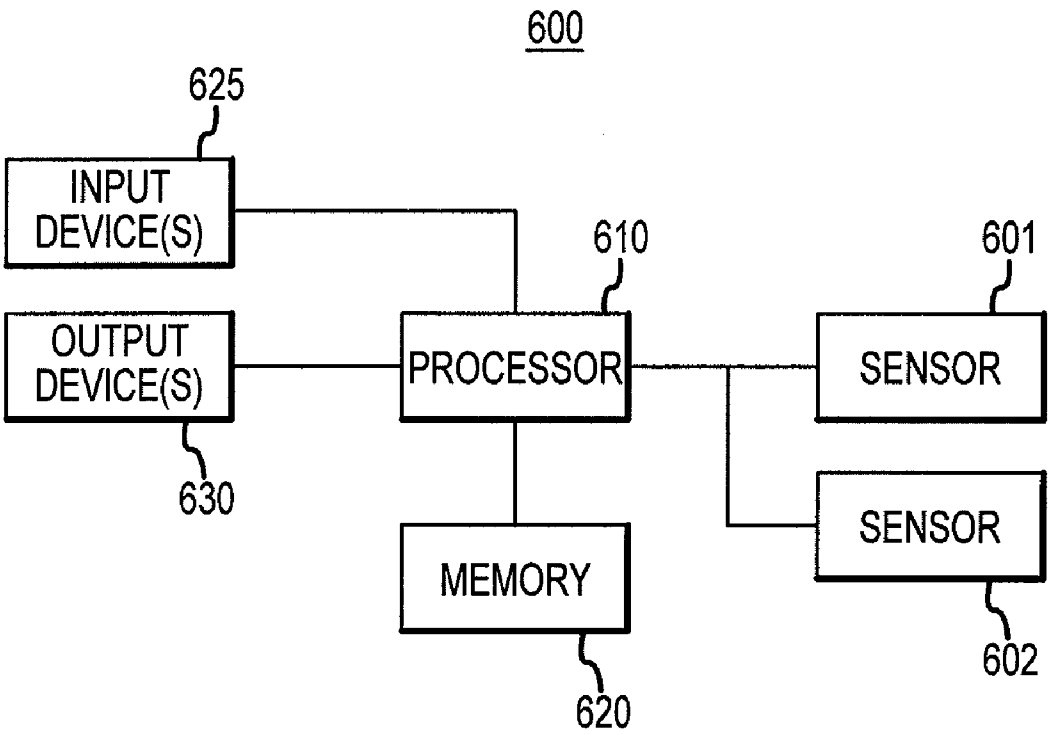
FIG. 6 depicts a device according to an embodiment of the present invention.

Accordingly, a system 600 according to an embodiment of the present invention is shown in FIG. 6. One or more sensors 601, 602 are positioned to measure force or displacement of a compression member that may, for example, be used to apply chest compressions. The sensors 601, 602 may be coupled to a processor 610 through any transmission medium, wired or wireless. The processor 610 may be configured to generate force-displacement curves as described above, parameterize the curves, and analyze the non-linearity of the curves, or any one of or combination of those acts. The processor 610 may be coupled to a memory 620 which may be encoded with a computer program including instructions causing the processor to receive measurements, generate force-depth relationships, or analyze force-depth curves as described above. The processor 610 may further be operable to receive inputs or send outputs to input or output devices 625, 630. An embodiment of an output device may include a feedback device to provide feedback to a rescuer as generally described above.

From the foregoing it will be appreciated that, although specific embodiments of the invention have been described herein for purposes of illustration, various modifications may be made without deviating from the spirit and scope of the invention.

What is claimed is:

1. A method for monitoring chest compressions performed using a compression member, the method comprising:
- measuring a force exerted by the compression member;
- measuring a displacement of the compression member;
- providing a chest stiffness function representing a relationship between force and displacement based in part on the measured force and the measured displacement;
- analyzing linearity of the chest stiffness function; and
- providing an indication of efficient chest compressions when operating in a non-linear part of the chest stiffness function.

2. The method according to claim 1, wherein the act of analyzing linearity comprises calculating a second derivative of the chest stiffness function.

3. The method according to claim 2, further comprising comparing the second derivative of the chest stiffness function to a threshold to assess linearity or non-linearity.

4. The method according to claim 1, wherein the act of analyzing linearity is based on an average or median of a predetermined number of compressions.

5. The method according to claim 1, wherein the chest stiffness function is determined by calculating and subtracting a damping force component from the measured force, the damping force being dependent in part on a velocity of the chest compression member.

6. The method according to claim 1, wherein the act of analyzing linearity includes fitting the measured chest stiffness function to a polynomial, exponential or spline function.

7. The method according to claim 1, further comprising providing an indication of patient category based on results of said linearity analysis, where a degree of non-linearity at least in part determines the patient category.

8. The method according to claim 7, wherein the indication of patient category distinguishes between patients of different age.

9. The method according to claim 7, wherein the indication of patient category distinguishes between patients of different chest size.

10. The method according to claim 7, wherein the indication of patient category distinguishes between patients lying on surfaces of different stiffness.

11. The method according to claim 1, further comprising providing an indication of a non-efficient compression when the non-liner part of the chest stiffness function does not exceed a predetermined value.

12. The method according to claim 1, wherein the chest stiffness function comprises a force-displaCement curve having a non-linear part and a linear part.

13. A device for monitoring chest compressions performed using a compression member, the device comprising:
- a first sensor configured to measure force exerted by the compression member;
- a second sensor configured to measure displacement of the compression member;
- a processor programmed to provide a chest stiffness funtion representing a relationship between force and displacement based on values derived from the measured force and the measured displacement, programed to analyze linearity of the chest stiffness function, and programmed to provide an indication of efficient chest compressions when operating in a non-linear part of the chest stiffness function.

14. The device according to claim 13, wherein the chest stiffness function comprises a force-displacement curve having a non-linear part and a linear part.

* * * * *